United States Patent [19]

Hilverda

[11] Patent Number: Plant 7,114

[45] Date of Patent: Jan. 16, 1990

[54] CARNATION NAMED HILSHOW

[76] Inventor: Jan J. Hilverda, 12 Stommeerweg, Aalsmeer, Netherlands

[21] Appl. No.: 308,647

[22] Filed: Feb. 10, 1989

[51] Int. Cl.[4] ..... A01H 5/00

[52] U.S. Cl. ..... Plt./71

[58] Field of Search ..... Plt./70–71

*Primary Examiner*—Robert E. Bagwill

*Attorney, Agent, or Firm*—Charles W. Rummler

[57] ABSTRACT

A new spray carnation cultivar particularly distinguished by its very short height and profuse production of very small pink blossoms, which grow in clusters on strong, upright flowering stems, the plant itself having a strong, vigorous, upright growth habit with abundant and rather dense foliage and being of such overall size as to be particularly adaptable for pot plant culture.

1 Drawing Sheet

BACKGROUND OF THE NEW PLANT

This new spray carnation variety originated as a seedling of a hybrid resulting from my crossing of two unnamed and unpatented carnation varieties selected from my collection of carnation plants maintained at my greenhouse for breeding purposes at Aalsmeer, The Netherlands, the object of this crossing being to develop new types of carnation plants so as to improve the range of varieties for commercial production and particularly plants which would have more rapid growth, better flower colors and an improved flower production rate. This particular seedling was selected by me for propagation because of its rapid growth habit, reaching a terminal height in a relatively short time, and because of its very abundant production of small, almost tiny, pink flowers. Propagation of this selected seedling was done by me at Aalsmeer by means of cuttings with such surprising and satisfactory results that I directed that this new carnation variety be propagated through several successive generations by means of cuttings at my Aalsmeer nursery. This extended propagation demonstrated conclusively that this new plant would maintain its distinctive characteristics from generation to generation and that its homogenetic character could be assured for commercial pot plant production.

DESCRIPTION OF THE DRAWING

My new spray carnation cultivar is illustrated by the accompanying photographic drawing which shows, in full color, the blooming portion of a flowering stem having a freshly opened bloom and buds in several stages of maturity, as well as a full face view of one of the flowers, together with several petals and a bud at the beginning of its opening stage, the colors shown being as nearly true to those herein specified as is reasonably possible to obtain by conventional photographic procedures.

DESCRIPTION OF THE NEW PLANT

The following is a detailed description of my new spray carnation cultivar based upon observations made during the current year at Aalsmeer, the color designations being according to The R.H.S. Colour Chart published by The Royal Horticultural Society of London, England.

THE PLANT

Origin: Seedling.

Parentage:

*Seed parent.*—An unnamed and unpatented carnation variety.

*Pollen parent.*—An unnamed and unpatented carnation variety. Both varieties having been selected by me from my collection of carnation varieties maintained by me at Aalsmeer for breeding purposes.

Classification:

*Botanic.*—*Dianthus caryophyllus* L.

*Commercial.*—Pot Carnation.

Form: An erect bush of very short height.

Height: Approximately 25 cm.

Growth habit: Rapid, strong, vigorous and upright.

Branching character: Alternate.

Foliage:

*Quantity.*—Abundant and considered to be dense.

*Size of leaf.*—Averages about 6 to 8 cm. in length.

*Leaf shape.*—Elliptical with acute apex and entire margins.

*Texture.*—Leathery.

*Color.*—Blue Green on both upper side and under side.

*Ribs and veins.*—The midrib is prominent.

*Leaflets.*—None.

THE BUD

Size: Small.

*Diameter.*—About 5 to 8 mm.

*Length.*—About 20 mm.

Shape: Cylindrical.

Opening rate: With mature buds, the flower petals show in about three to four days.

Color of petals: When sepals first divide: Pink. When petals begin to unfurl: Pink with a Red heart.

Sepals:

*Number.*—Five.

*Shape.*—Long ovate with acuminate tip.

*Character.*—The sepals are hooded over the bud before dividing and stand up as the flower petals unfurl.

*Color.*—Inside: Light green. Outside: Dark green.

*Striae.*—None.

Calyx:

*Size.*—Long.

*Shape.*—Cylindrical.
*Splitting.*—The calyx does not split.
*Aspect.*—Smooth.

Flowering stem:
*Length.*—Approximately 20 to 25 cm.
*Character.*—Rigid and erect.
*Color.*—Dark green.

THE FLOWER

Blooming habit: Continuous with profuse flower production.

Size of bloom: Very small.
*Diameter.*—Approximately 30 mm., in average.
*Depth.*—Approximately 10 to 12 mm., in average.

Borne: In clusters on straight, upright stems emitted in longitudinally-spaced relation from a very short, strong and erect flowering stem.

Flower shape: When bloom first opens, the bloom has a high center. When bloom matures, it tends to flatten.

Petalage:
*Number of petals.*—Averages from about five to eight.
*Arrangement.*—Imbricated.
*Form.*—Fan-shaped with dentated margin and rounded end.
*Texture.*—Soft.
*Appearance.*—Velvety.
*Color.*—All petals have the same coloration with the outer half of the petal body being Pink, Empire Rose to Carmine Rose, R.H.S. 48D/52D, with Claret Rose picotee, R.H.S. 50A, along the entire inner margin of the generally Pink body portion of the petal, the inner half portion of each petal being White, R.H.S. 155-D, for its entire length.

Flower stem:
*Length.*—Approximately 20 cm.
*Color.*—Dark green.
*Character.*—Sturdy and upfight.

Discoloration after full bloom: None.

Fragrance: Weak.

Persistence: The flowers hang on and dry.

Lasting quality: On the plant, about 14 to 21 days either as a pot plant or a bedding plant.

REPRODUCTIVE ORGANS

Stamens:
*Number.*—8 to 10.
*Arrangement.*—Evenly around the ovary.
*Anthers.*—Size: Small. Color: Cream White.
*Filaments.*—Length: About 15 to 20 mm. Color: White with pinkish top.
*Pollen.*—Color: White.

Pistils:
*Number.*—One.
*Style.*—Length: Approximately 20 mm. Color: White with pinkish top.
*Stigma.*—Color: White to light pink.

Character of ovaries: Normal.

This new variety of carnation most nearly resembles the pot carnation 'Pinki' (unpatented) but is distinguished from 'Pinki' by its color, its more compact growth and its higher flower production.

I claim:

1. A new and distinct spray carnation variety, substantially as herein shown and described, characterized by its very small, generally pink flowers borne in clusters on a strong stem from a plant of very short height and particularly adaptable to pot plant culture.

* * * * *

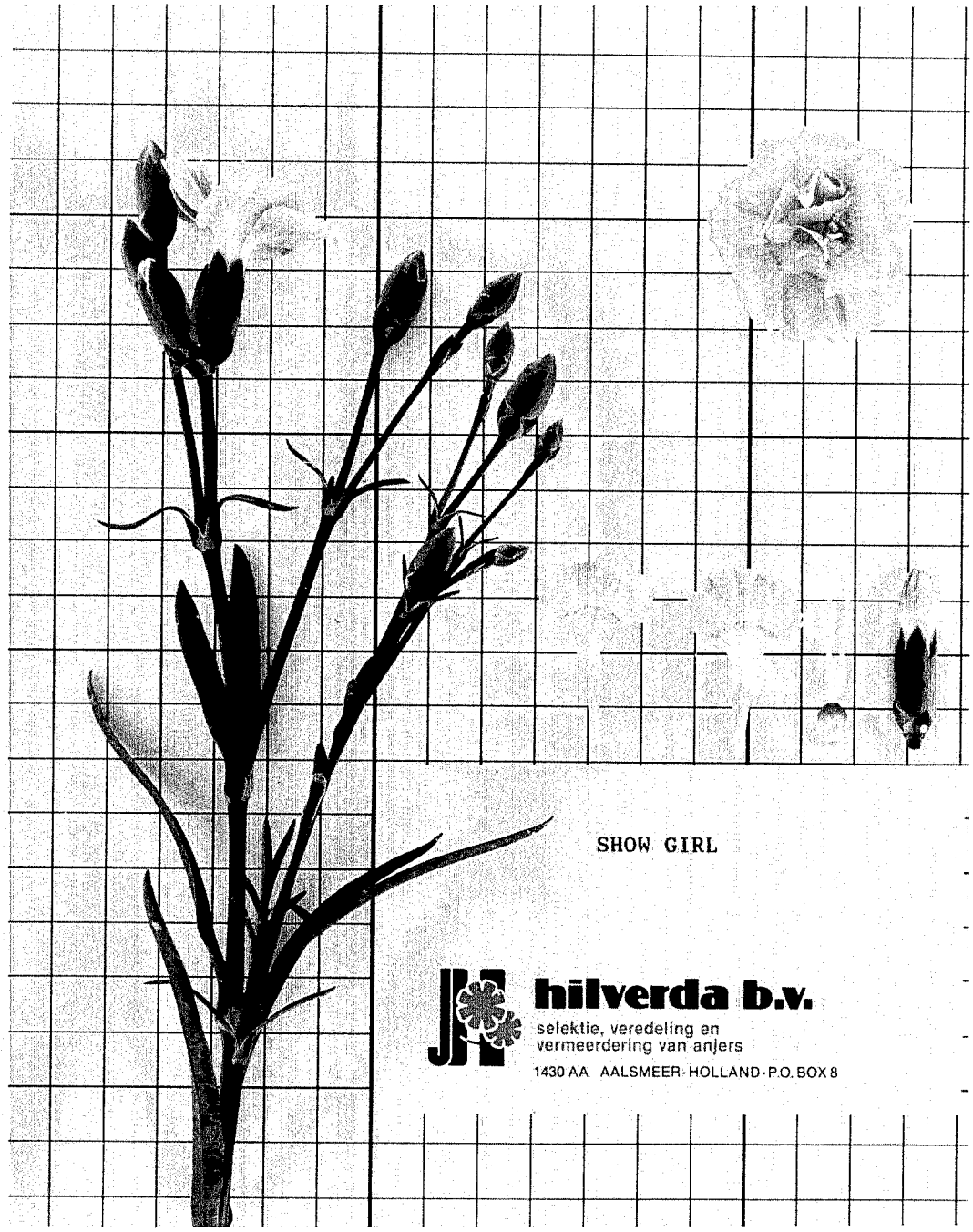
SHOW GIRL
hilverda b.v.
selektie, veredeling en
vermeerdering van anjers
1430 AA AALSMEER-HOLLAND-P.O. BOX 8